(12) United States Patent
Power et al.

(10) Patent No.: US 8,826,911 B2
(45) Date of Patent: Sep. 9, 2014

(54) BARRIER PROTECTION USING LINEAR TEAR TECHNOLOGY

(76) Inventors: David Power, Elma, NY (US); David Nowicki, Lancaster, NY (US)

( * ) Notice: Subject to any disclaimer, the term of this patent is extended or adjusted under 35 U.S.C. 154(b) by 96 days.

(21) Appl. No.: 13/289,184

(22) Filed: Nov. 4, 2011

(65) Prior Publication Data

US 2013/0112211 A1     May 9, 2013

(51) Int. Cl.
*A61F 5/37*     (2006.01)
*A61B 19/08*     (2006.01)
*A61B 19/00*     (2006.01)

(52) U.S. Cl.
CPC ........... *A61B 19/08* (2013.01); *A61B 2019/085* (2013.01); *A61B 2019/307* (2013.01)
USPC ............ 128/849; 128/850; 128/853; 128/854

(58) Field of Classification Search
USPC .................................................. 128/849–856
See application file for complete search history.

(56) References Cited

U.S. PATENT DOCUMENTS

| | | | | |
|---|---|---|---|---|
| 3,926,185 | A * | 12/1975 | Krzewinski | 128/854 |
| 5,975,082 | A * | 11/1999 | Dowdy | 128/849 |
| 6,286,511 | B1 | 9/2001 | Levitt et al. | |
| 6,405,730 | B2 | 6/2002 | Levitt et al. | |
| 2008/0006279 | A1 * | 1/2008 | Bodenham et al. | 128/853 |
| 2010/0031966 | A1 * | 2/2010 | Allen | 128/851 |

* cited by examiner

*Primary Examiner* — Patricia Bianco
(74) *Attorney, Agent, or Firm* — Kloss, Stenger, LoTempio; Vincent G. LoTempio; David Stephenson

(57) ABSTRACT

A surgical drape comprising a base sheet defining a base sheet aperture, an absorbent pad attached to the base sheet and defining a pad aperture positioned in substantial alignment with the base sheet aperture, and a linear tear polymer pane attached to the base sheet and absorbent pad and defining a fenestration in substantial alignment with the base sheet and pad apertures. The base sheet, absorbent pad and linear tear polymer pane are operatively arranged to tear in communication with one another when the drape is torn away from a patient. The linear tear polymer pane further and has an adhesive strip to adhere the drape to the patient's body when the drape is in position during surgery.

6 Claims, 3 Drawing Sheets

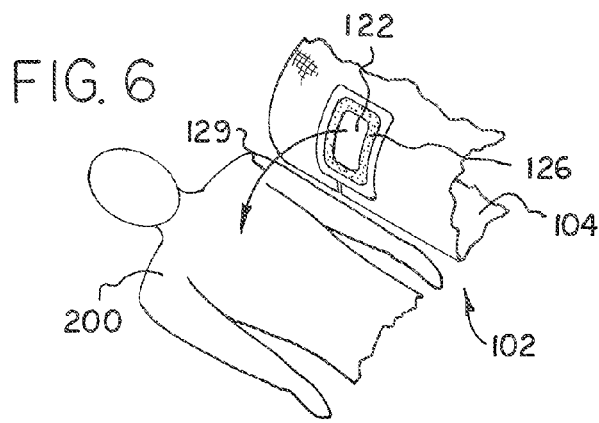
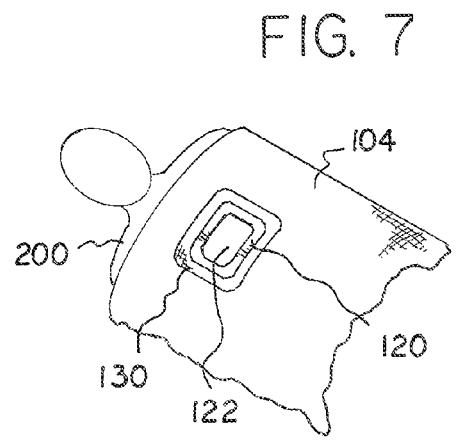
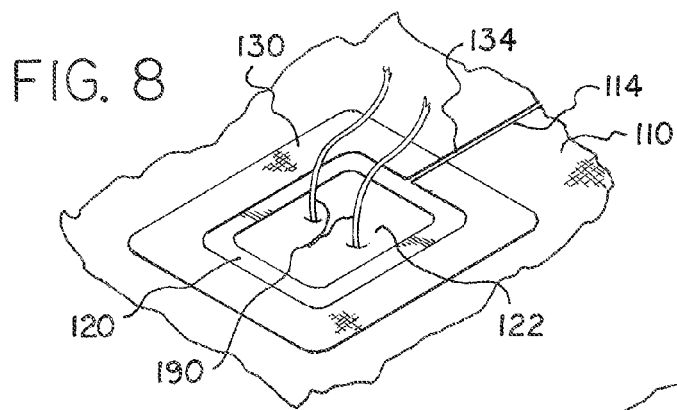
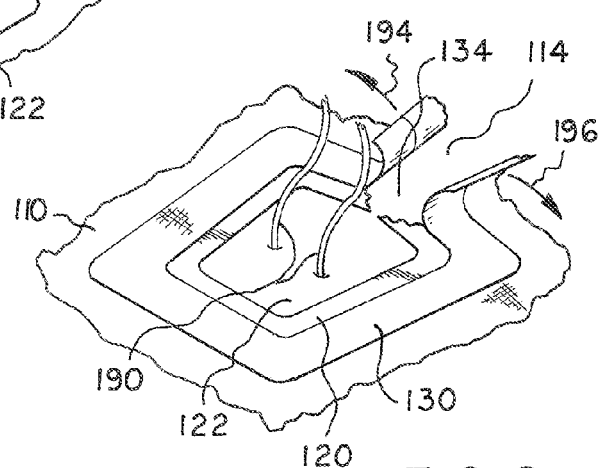
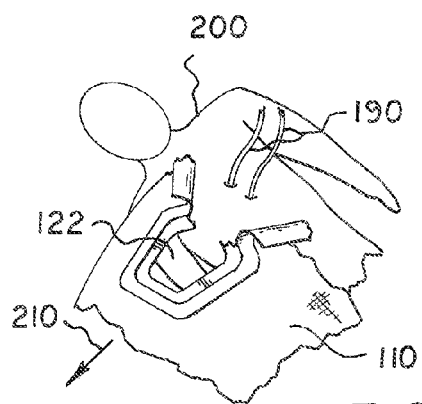

BARRIER PROTECTION USING LINEAR TEAR TECHNOLOGY

BACKGROUND OF THE INVENTION

1. Field of the Invention

This patent application pertains to medical drapes, and more specifically, pertains to fenestrated surgical drapes. Even more specifically, this patent application relates to fenestrated surgical drapes that allow for removal of the drape from a patent following surgery without first requiring removal of tubes or catheters from the patient.

2. Background

Medical drapes are used in various applications in operating rooms, cardiac catheterization departments and other departments throughout healthcare facilities. The main purpose of the medical drapes is to provide a sterile field about the surgical site and to cover the patient during an invasive procedure. Typical surgical drapes have one or more openings or windows commonly known in the medical field as a "fenestrated incision site."

Medical drapes are intended to maintain a sterile field around a fenestrated incision site, maintaining a barrier that minimizes the passage of microorganisms between the non-sterile and sterile areas. Fenestrated medical drapes are commonly made of disposable nonwoven fabrics, plastic polymeric film or perforated papers all of which surround the incision site.

Current problems with medical drapes occur during the removal of the soiled medical drape where medical apparatus such as wires, tubes, blood pumps, and the like, remain in the patient after a medical procedure is performed. Because such medical apparatus is received into the body through the apertures in the surgical drape, it is a problem to remove the drape after the procedure has been completed. Although the base sheet is often made of an easy-to-tear material, the stronger plastic polymeric film or absorbent pads usually require the use of scissors or perforations to be remove the drape from the patient. Obviously, the preferred medical practice is to avoid the use of scissors to remove the surgical drape. Existing designs to solve this problem of drape removal is to use perforations in the various components of the drape. Perforations help to make removal easier but in doing so the perforations compromise the sterile field protection that the drape is designed to offer.

Others have tried to solve the drape removal problem mainly by either using specialized perforations or by leaving the polymer layer unperforated. However, while the unperforated polymer layer does give protection and provides a barrier against micro-organisms, the lack of perforations makes removal of the drape difficult. The use of perforations solves the problem of easy removal of the drape, but compromises the sterile field protection because there are holes made in the drape.

U.S. Pat. No. 5,975,082 issued to Dowdy discloses a tear away surgical drape with an opening surrounded by a perforated absorbent pad. The drape and pad have a perforated score line for tearing away the pad after surgery. The tear-away perforation allows the drape to be torn and removed without use of scissors and without the need of removing the tube or catheter from the patient. However, the perforations destroy the sterile field between the drape and the environment and increase risks for contamination and infection.

U.S. Pat. Nos. 6,286,511 and 6,405,730 both issued to Levitt et al. provide an ophthalmic drape having integral, perforated tear lines. The drape has a fenestration for allowing access to the eye, with an absorbent pad encircling the opening. One set of tear lines permits the drape to be torn in two halves while an alternative set of tear lines are set at an oblique angle to tear out a small portion of the drape. The Levitt patents are similar to the Dowdy patent discussed above as each discuss a drape having perforated tear lines. As such, the perforations destroy the sterile field between the drape and the environment and increase risks for contamination and infection.

United States patent application publication number 2010/0031966 to Allen provides a medical drape having a score line between a fenestration and the outer edge of the drape. The score line is secured using an adhesive strip. After use, the adhesive strip is removed exposing the score line. The score line allows separation of the two halves of the drape such that a catheter or tube does not have to be removed from the patient after surgery or treatment. The Allen application is another variation of a tear-away drape. Importantly, the Allen drape is split and reattached before use thereby increasing production time and cost as more materials and production steps are needed to produce the final device. Moreover, the additional steps and materials increase the risk of contamination. Furthermore, the removal of the adhesive material may cause the adhesive strip to contact and stick to the drape, patient, or other materials leading to dangerous conditions in the surgical or treatment area.

Thus, it is readily apparent that there is a long-felt need for a sterile, non-perforated fenestrated surgical drape which can be easily removed from a patient's body after completion of a surgical procedure.

The present invention seeks to alleviate the problems associated with the fenestrated surgical drapes that allow for removal of the drape from a patent following surgery without first requiring removal of tubes or catheters from the patient and to provide a device that maintains a sterile field between the patient and the environment.

SUMMARY OF THE INVENTION

It is the object of the disclosure to provide a surgical drape having barrier protection while offering simple removal through use of linear tear film technology that maintains an absolute barrier for the patient during a surgical procedure.

It is another object of the disclosure to provide a fenestration aperture encircled by linear tear film that tears in a straight line due to its molecular design.

Yet another object of the invention is to provide a surgical drape which allows for easier removal from the patient after a surgical procedure while still providing a barrier of protection for the patient against infection.

The objects of the present disclosure are achieved by provision of a surgical drape consisting of a large rectangular base sheet of non-woven material with a piece of absorbent reinforcement pad in the center and a fenestration provided within the base sheet and pad. The fenestration is encircled by a non-perforated, linear tear polymer film. A tear line extends proximate one end of the drape to the external edge of the linear tear film.

The above and other objects are accomplished in accordance with the present invention which comprises a fenestrated surgical drape which employs linear tear polymer technology. The linear tear polymer is molecularly designed to tear evenly in a straight line with ease without the use of instruments such as scissors. The linear tear polymer does not require perforations to direct the tear in a straight line, thus the linear tear polymer component allows for easy removal and does not compromise the sterile barrier of protection for the patient. The use of linear tear film technology is a much needed improvement over existing designs which resolve only one of two problems: ease of tearing and maintaining a sterile barrier. The present disclosure solves both existing problems at the same time.

The surgical drape of the present disclosure has an overall appearance consisting of a large rectangular piece of non-woven base sheet with an absorbent reinforcement pad in the center and a fenestration cut within the pad and base sheet. In the present disclosure, the fenestration is further encircled by a polymer film. The surgical drape of the present disclosure is comprised of various components for different uses in the operating room. The base sheet of the surgical drape is comprised of commonly used medical drape material such as SMS (Spunbond-Meltblown-Spunbond) material or spunlace material, both materials being a type of non-woven fabric. The surgical drape of the present disclosure is further equipped with a fenestration which allows access to the surgical site of the patient. The fenestration is encircled with a linear tear film. The linear tear film material maintains a sterile field around the incision site while also making removal of the drape easier than previous designs.

Although the anticipated preferred embodiment for the device of the present disclosure is comprised of a linear tear film material that maintains a sterile field around the incision site while also making removal of the drape easier than previous designs an optional, additional component is the addition of an absorbent reinforcement material surrounding the fenestration.

DESCRIPTION OF THE DRAWINGS

The nature and mode of operation of the present disclosure and the manner in which it may be practiced will now be more fully described in the following detailed description and is further illustrated with reference to the accompanying drawings wherein:

FIG. 6 is a perspective view of a surgical drape of one embodiment of the present disclosure showing the adhesive side of linear tear film window being placed on a patient.

FIG. 7 is a perspective view of a surgical drape of one embodiment of the present disclosure showing the drape on a surgery patient.

FIG. 8 is an expanded view of a surgical drape of one embodiment of the present disclosure showing the drape on a patient with tubes and/or catheters extending through a fenestration window.

FIG. 9 is an expanded view of a surgical drape of one embodiment of the present disclosure showing a pane being pulled apart without disturbing the tubes and/or catheters.

FIG. 10 is a perspective view of a surgical drape of one embodiment of the present disclosure showing the removal of the drape from a patient after surgery.

DETAILED DESCRIPTION OF THE INVENTION

Figure 1:
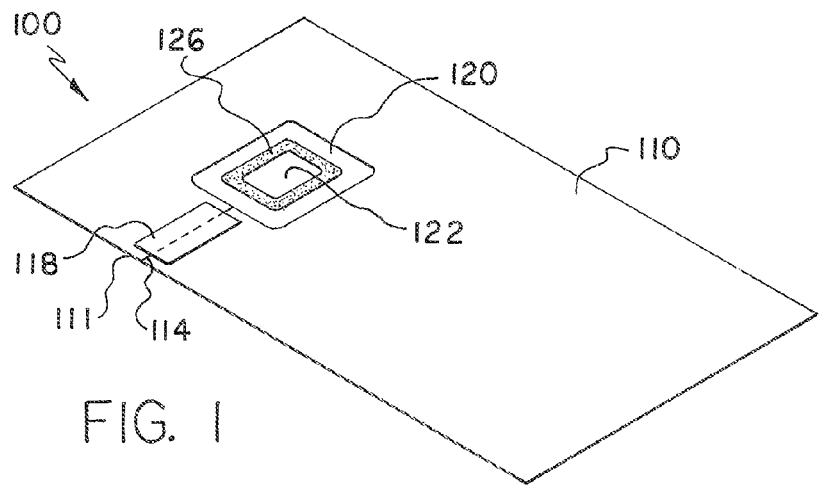
FIG. 1 is a perspective view of a surgical drape of one embodiment of the present disclosure with the adhesive side of the fenestration facing up.

At the outset, it should be clearly understood that like reference numerals are intended to identify the same structural elements, portions, or surfaces consistently throughout the several drawing figures, as may be further described or explained by the entire written specification of which this detailed description is an integral part. The drawings are intended to be read together with the specification and are to be construed as a portion of the entire "written description" of this invention as required by 35 U.S.C. §112.

The present disclosure seeks to alleviate the problems associated with the fenestrated surgical drapes having perforated tear lines that do not maintain a sterile environment. The present disclosure provides for an apparatus which comprises a fenestrated surgical drape which employs linear tear polymer technology that allows for removal of the drape from a patent following surgery without first requiring removal of tubes or catheters from the patient and to maintain a sterile field between the patient and the environment.

Adverting now to the drawings, with reference to FIG. 1, an embodiment of a surgical drape of the present disclosure is indicated generally by numeral 100. Surgical drape 100 for covering a patient's body during surgery comprises a base sheet 110 having at least one edge and at least one drape cut or tear line 114 having a starting point along edge 111 extending in a direct line to an aperture or open fenestration 122 defined by linear tear film pane 120 for surrounding a surgical site on the patient's body attached to the base sheet and operatively arranged to tear in communication with tear line 114 when the drape is torn away from a patient. The pane defines fenestration 122 for surrounding a surgical site on the patient's body and is positioned on the base sheet so that the aperture on base sheet 110 and the fenestration on the pane are in substantial alignment. Tear line 114 extends from outer edge 111 of base sheet 110 to exterior edge of linear tear film pane 120. As shown, an embodiment of tear line 114 is a drape cut extending completely through the thickness of base sheet 110. Alternative tear lines are envisioned such as but not limited to perforations, slits, and the like.

Tear cover panel 118 is removably attached to base sheet 110 and is used to secure base sheet 110 on either side of tear line 114 during surgery. The top surface of linear tear film pane 120 is equipped with adhesive strips 126 proximate fenestration 122. Adhesive strips 126 secure the drape onto the patient and provide a sterile barrier around fenestration 122. Although surgical drape 100 is shown as a rectangular sheet, certainly this shape is not exhaustive and it should be appreciated that other suitable shapes and dimensions other than those illustrated are used as surgical drape 100 for the present disclosure. Similarly, fenestration 122 can be constructed in varying sizes and shapes to more suit a particular surgical need. For instance, the fenestration may be a relatively small, oval aperture for use in laparoscopic procedures while being a relatively large, rectangular aperture when conducting open chest surgery which requires insertion of tubes into a patient's body.

Figure 2:
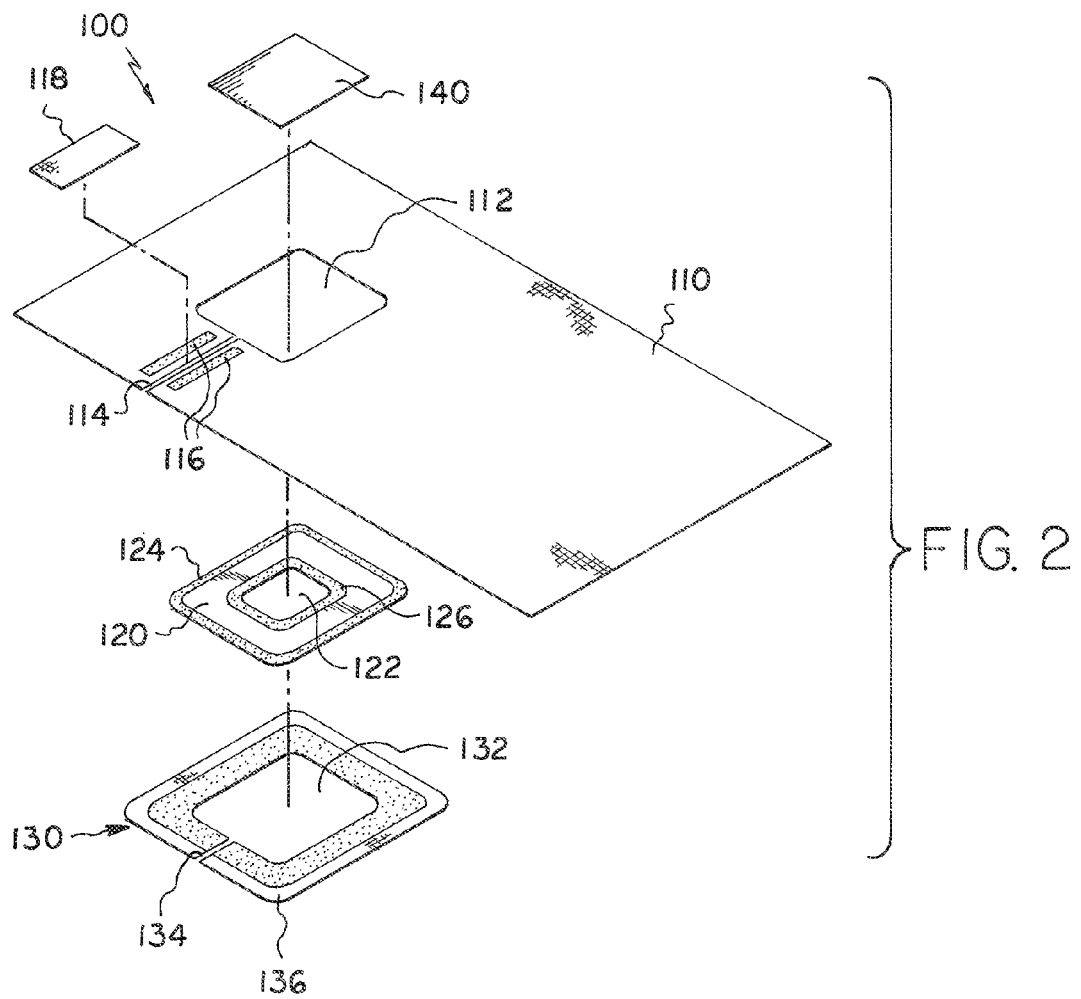
FIG. 2 is an exploded view of a surgical drape of one embodiment of the present disclosure.

FIG. 2 shows an exploded view of a surgical drape of one embodiment of the present disclosure. Surgical drape 100 is generally comprised of base sheet 110, linear tear film pane 120 and absorbent pad 130. In a preferred embodiment, base sheet 110 is constructed as a generally rectangular member of any suitable material, and more preferable of a non-woven material such as SMS or spunlace fabric. Cut into base sheet 110 is pane aperture 112. Tear line 114 extends from pane aperture 112 to the periphery of base sheet 110. Although shown as a completed cut, it is envisioned that tear line 114 is comprised of a plurality of perforations thereby easing tearing of base sheet 110. The two halves of base sheet 110 are releasably affixed to one another by tear cover panel 118 and adhesive strips 116.

Affixed to base sheet 110 is linear tear film pane 120. Linear tear film pane 120 has a general shape which corresponds with pane aperture 112 but has a slightly larger circumference. The larger circumference is used to secure linear tear film pane 120 to base sheet 110 such that pane 120 surrounds pane aperture 112 and extends partially within pane aperture 112 to form fenestration 122. While any suitable fastening means can be used, in a preferred embodiment, the outer edge of linear tear film pane 120 is furnished with adhesive 124 for affixing linear tear film pane 120 to base sheet 110. The adhesive strip is provided to adhere the drape to the patient's body when the drape is in position during surgery. Linear tear film pane 120 is further equipped with adhesive strips 126 proximate fenestration aperture 122. Linear tear film pane 120 is constructed such that adhesive 124 circumscribes pane aperture 112 to form a complete seal between pane 120 and base sheet 110 while adhesive strips 126 are interposed within pane aperture 112 and do not contact base sheet 110. In this arrangement, fenestration 122 is in fluid communication with pane aperture 112.

Release 140 is removably affixed to linear tear film pane 120 by provision of adhesive strips 126. When in use, release 140 is removed and the drape is position on the patient such that adhesive strips 126 contact the patient and form a barrier between the sterile surgical site and the non-sterile exterior environment.

In a preferred embodiment, surgical drape 100 is further comprised of absorbent pad 130 which circumscribes linear tear film pane 120. Absorbent pad 130 has a pad aperture 132 which corresponds to and is substantially aligned with pane aperture 112 and fenestration 122. Pad linear tear 134 extends from pad aperture 132 to the periphery of absorbent pad 130. During fabrication, linear tear 134 is positioned such that it aligns and overlaps with linear tear 114 thereby ensuring easy tearing of the drape. Absorbent pad 130 is affixed to base sheet 110 by way of adhesive 136 located proximate the outer circumference of pad 130. Although described as being constructed with adhesive strips forming sealed connections between the base sheet, linear tear film pane and absorbent pad, alternative construction and sealing means can be employed, such as but not limited to heat sealing, ultra sonic welding, and gluing.

Figure 3:
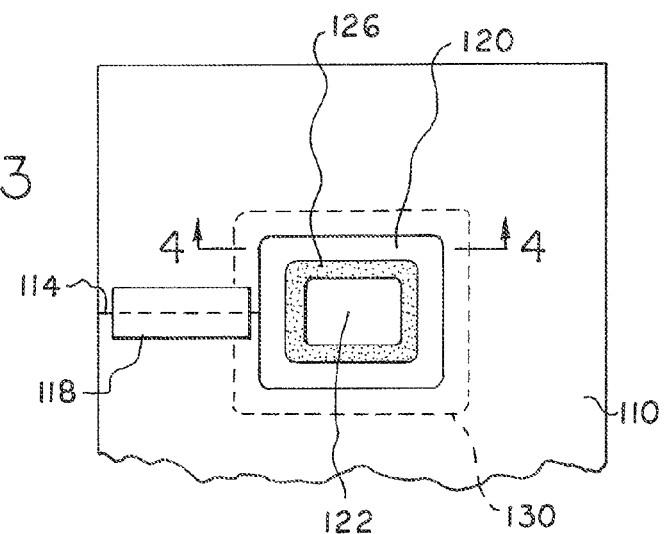
FIG. 3 is a top view of a surgical drape of one embodiment of the present disclosure with the adhesive side of the fenestration facing up.

FIG. 3 is a top view of a surgical drape of one embodiment of the present disclosure with the adhesive side of the fenestration facing up. As shown, base sheet 110 has linear drape cut or tear 114 extending from the periphery of base sheet 110 to the outer edge of linear tear film pane 120. The drape cut extends completely through a thickness of the base sheet such that two adjoining cut edges are completely severed from one another to permit easy separation of the two adjoining cut edges. The two halves of linear tear 114 are releasably secured by provision of tear cover panel 118. Linear tear film pane 120 defines fenestration 122 through which surgical or other medical procedures are performed. The open region of fenestration 122 is circumscribed by linear tear film pane 120 having adhesive strips 126. The drape cut has a first adhesive tape strip positioned along one of the two adjoining cut edges, a second adhesive tape strip positioned along a second edge of the two adjoining cut edges, and a length of drape material releasably affixed to the adhesive tape strips to secure the two adjoining cut edges to each other. Adhesive strips 126 are used to removably attach the surgical drape to the patient during a medical procedure. Absorbent pad 130 is shown in broken lines for reference as it lies on the underside of base sheet 110 and linear tear film pane 120.

Figure 4:
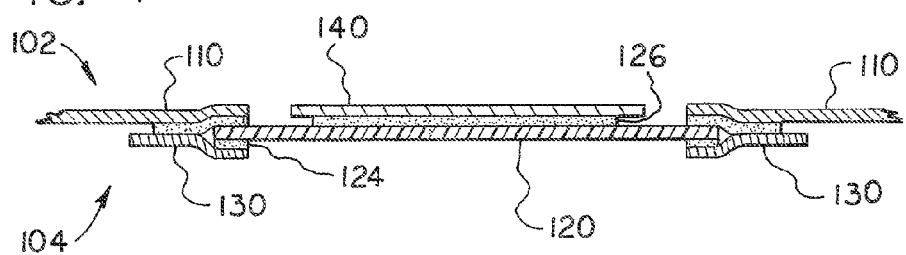
FIG. 4 is an enlarged cross sectional view of a surgical drape of one embodiment of the present disclosure taken generally across arrows 4-4 of FIG. 3.

FIG. 4 is an enlarged cross sectional view of a surgical drape of one embodiment of the present disclosure taken generally across arrows 4-4 of FIG. 3. Surgical drape 100 (see FIGS. 1 and 2) has a front side 102 which faces the patient and is adhered to the patient's body when in use, and a back side 104 which faces away from the patient. Front side 102 is comprised generally of base sheet 110. Below base sheet 110 is linear tear film pane 120. Linear tear film pane 120 is affixed to base sheet 110 using any suitable means heat sealing, such as ultra sonic welding, taping, and gluing, but in a preferred embodiment the means is an adhesive strip 124. Absorbent pad 130 is the final layer of back side 104 around pane aperture 112 (see FIG. 2). Absorbent pad 130 is affixed to base sheet 110 and the outer portion of linear tear film pane 120. The absorbent pad is attached to the base sheet and is operatively arranged to tear in communication with the drape cut when the drape is torn away from a patient. The absorbent pad defines an aperture for surrounding a surgical site on the patient's body and is positioned on the base sheet so that the aperture on the base sheet and the aperture on the absorbent pad and the fenestration on the pane are in substantial alignment.

While any suitable means can be used to affix the absorbent pad such as heat sealing, ultra sonic welding, taping, and gluing, in a preferred embodiment this means is an adhesive strip 136. Release 140 is removably attached to linear tear film pane 120 by use of adhesive strip 126. Release 140 covers fenestration 122 and protects adhesive strip 126 when surgical drape 100 is not in use. Once release 140 is removed for use, adhesive strip 126 is pressed onto a patient to help secure surgical drape 100 on the body and provide a barrier between the sterile surgical site and the non-sterile environment.

Figure 5:
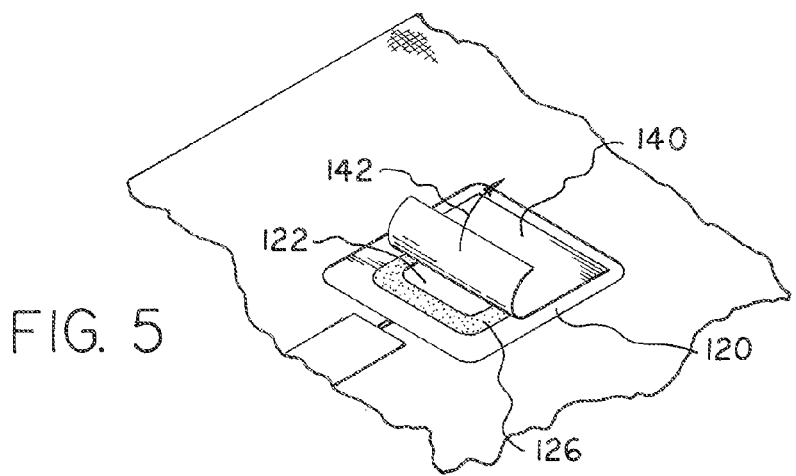
FIG. 5 is a top perspective view of a surgical drape of one embodiment of the present disclosure showing the release paper being removed from the fenestration.

FIG. 5 is a top perspective view of a surgical drape of one embodiment of the present disclosure showing the release paper being removed from the fenestration. Release 140 is simply peeled away, in the general direction shown by arrow 142 from adhesive strip 126 on linear tear film pane 120 to reveal fenestration 122.

FIG. 6 is a perspective view of a surgical drape of one embodiment of the present disclosure showing the adhesive side of linear tear film window being placed on a patient. Once release 140 is removed from surgical drape 100, front side 102 is draped over patient 200 as shown generally by arrow 129. Fenestration 122 is positioned over the body at the site of the surgical procedure to be performed. Adhesive strip 126 releasably secures surgical drape 100 to patient 200.

FIG. 7 is a perspective view of a surgical drape of one embodiment of the present disclosure showing the drape on a patient for surgery. Back side 104 of surgical drape 100 faces outwardly toward medical personnel. Fenestration 122 is position over a surgical site and is surrounded by linear tear film pane 120. Absorbent pad 130 circumscribes linear tear film pane 120 and is used to collect any fluids which are produced during surgery.

FIG. 8 is an expanded view of a surgical drape of one embodiment of the present disclosure showing surgical drape 100 on a patient with tubes and/or catheters 190 extending through fenestration 122. As shown in FIG. 8, base sheet 110 has a linear tear 114 which corresponds with pad linear tear 134 of absorbent pad 130, both of which lead to the outer edge of linear tear film pane 120.

FIG. 9 is an expanded view of a surgical drape of one embodiment of the present disclosure showing surgical drape 100 being pulled apart in the general direction as shown by arrows 194 and 196 without disturbing tubes and/or catheters 190. Base sheet 110 is separated by pulling away the two ends of the sheet on either side of linear tear 114. Similarly, absorbent pad 130 is separated by pulling away the two ends of the pad on either side of pad linear tear 134. Linear tear film pane 120 does not have a tear line, but through its specially molecularly designed linear tear properties, linear tear film pane is pulled apart so that surgical drape 100 is separated from the external periphery of base sheet 110 through to fenestration 122.

FIG. 10 is a perspective view of a surgical drape of one embodiment of the present disclosure showing the removal of the drape from a patient after surgery. Once surgical drape 100 has been separated from the external periphery of base sheet 110 through to fenestration 122, the drape can then be removed from patient 200 in the general direction of arrow 210 without disturbing or first requiring the removal of tubes and/or catheters 190.

Although the invention has been described with reference to certain preferred embodiments, it will be appreciated by those skilled in the art that modifications and variations may be made without departing from the spirit and scope of the invention. It should be understood that applicant does not intend to be limited to the particular details described above and illustrated in the accompanying drawings.

The invention claimed is:

1. A surgical drape for covering a patient's body during surgery comprising:
a base sheet having at least one edge, said base sheet defining at least one aperture therein and said base sheet having at least one drape cut having a starting point along said at least one edge and extending in a line to said aperture;
a pane comprised of a linear tear film that does not have perforations attached to said base sheet and operatively arranged to tear in communication with said at least one drape cut when said drape is torn away from a patient, said pane defining at least one fenestration for surrounding a surgical site on said patient's body and positioned on said base sheet so that said aperture on said base sheet and said at least one fenestration in said pane are in substantial alignment.

2. The surgical drape of claim 1 wherein said pane has an adhesive strip to adhere to the patient's body when the drape is in position during surgery.

3. The surgical drape of claim 1 wherein said drape cut extends completely along said base sheet such that two adjoining cut edges are completely severed from one another to permit easy separation of said two adjoining cut edges.

4. The surgical drape of claim 1 wherein said at least one drape cut has a first adhesive tape strip positioned along one of said two adjoining cut edges, a second adhesive tape strip positioned along a second edge of said two adjoining cut edges, and a length of drape material releasably affixed to said adhesive tape strips to removably secure said two adjoining cut edges to each other.

5. The surgical drape of claim 1 further comprising an absorbent pad attached to said base sheet and operatively arranged to tear in communication with said at least one drape cut when said drape is torn away from a patient, said absorbent pad defining at least one aperture for surrounding a surgical site on said patient's body and positioned on said base sheet so that said aperture on said base sheet and said aperture on said absorbent pad and said fenestration on said pane are in substantial alignment.

6. A surgical drape for covering a patient's body during surgery comprising:
a base sheet having at least one edge, said base sheet defining at least one aperture therein and said base sheet having at least one drape cut having a starting point along said at least one edge and extending in a line to said aperture;
an absorbent pad attached to said base sheet and operatively arranged to tear in communication with said at least one drape cut when said drape is torn away from a patient, said absorbent pad defining at least one aperture for surrounding a surgical site on said patient's body and positioned on said base sheet so that said aperture on said base sheet and said aperture on said absorbent pad are in substantial alignment;
a pane attached to said base sheet and operatively arranged to tear in communication with said at least one drape cut when said drape is torn away from a patient, said pane defining at least one fenestration for surrounding a surgical site on said patient's body and positioned on said base sheet so that said aperture on said base sheet and said aperture on said absorbent pad and said at least one fenestration in said pane are in substantial alignment;
said drape cut extends completely along said base sheet such that two adjoining cut edges are completely severed from one another to permit easy separation of said two adjoining cut edges; and said at least one drape cut has a first adhesive tape strip positioned along one of said two adjoining cut edges, a second adhesive tape strip positioned along a second edge of said two adjoining cut edges, and a length of drape material releasably affixed to said adhesive tape strips to removably secure said two adjoining cut edges to each other; and wherein said pane is comprised of a linear tear film and has an adhesive strip to adhere to the patient's body when the drape is in position during surgery.

* * * * *